United States Patent [19]

Nagasawa et al.

[11] Patent Number: 4,940,816

[45] Date of Patent: Jul. 10, 1990

[54] ACYLATED CYANAMIDE COMPOUNDS

[75] Inventors: Herbert T. Nagasawa, Richfield, Minn.; Chul-Hoon Kwon, Rochester, N.Y.

[73] Assignee: Regents of the University of Minnesota, Minneapolis, Minn.

[21] Appl. No.: 382,554

[22] Filed: Jul. 19, 1989

Related U.S. Application Data

[62] Division of Ser. No. 110,790, Oct. 21, 1987, Pat. No. 4,870,056, which is a division of Ser. No. 821,604, Jan. 23, 1986, Pat. No. 4,726,941.

[51] Int. Cl.$^5$ ............................................ C07C 125/08
[52] U.S. Cl. ..................................... 564/103; 564/106
[58] Field of Search ................ 564/103, 106; 514/810, 514/811, 609

[56] References Cited

U.S. PATENT DOCUMENTS

| | | | |
|---|---|---|---|
| 4,368,206 | 1/1983 | Revici | 424/312 |
| 4,595,782 | 6/1986 | Hase | 564/103 |
| 4,726,941 | 2/1988 | Nagasawa | 514/19 |
| 4,870,056 | 9/1989 | Nagasawa | 514/19 |

FOREIGN PATENT DOCUMENTS

| | | |
|---|---|---|
| 0212744 | 6/1956 | Australia . |
| 0084836 | 8/1983 | European Pat. Off. . |
| 0087394 | 8/1983 | European Pat. Off. . |
| 2747472 | 4/1979 | Fed. Rep. of Germany . |

OTHER PUBLICATIONS

T. Mukaiyama et al., Chem. Abstr., 84 17345y (1976).
T. Taguchi, Chem. Abstr., 81, 37509w (1974).
C. H. Kwon and F. N. Shirota et al., The Pharmacologist, 27, 283 (Aug. 1985).
F. N. Shirota et al., Drug Megabolism and Disposition, 12, 337 (1984).
J. E. Peachey et al., Pharmac. Ther., 15, 89 (1981).
E. B. Truitt, Jr., et al., Proeeeding of the First Annual Alcoholism Conference of the National Institute on Alcohol Abuse and Alcoholism, Drew Publication No. (NHH) 74–675 (1973), pp. 100–111.

Primary Examiner—F. T. Moezie
Attorney, Agent, or Firm—Merchant, Gould, Smith, Edell, Welter & Schmidt

[57] ABSTRACT

Acylated cyanamide compounds useful for ethanol deterrence of the formula RCONHCN, wherein R is a lipophilic acyl group or is derived from an (N-substituted)-alpha-aminoacyl group.

2 Claims, 6 Drawing Sheets

ACYLATED CYANAMIDE COMPOUNDS

BACKGROUND OF THE INVENTION

This invention was made in part with the assistance of grants from the Veterans Administration. The government has certain rights in this invention.

This application is a divisional of Ser. No. 7/110,790, filed Oct. 21, 1987, now U.S. Pat. No. 4,870,056, which is a divisional of Ser. No. 06/821,604, filed Jan. 23, 1986, now U.S. Pat. No. 4,726,941.

The alcohol sensitizing drugs disulfiram (tetraethylthiuram disulfide; Antabuse ®) and carbimide (citrated calcium carbimide; Temposil ®) increase blood acetaldehyde concentrations in the presence of ethanol by inhibiting the oxidation of acetaldehyde to acetic acid by aldehyde dehydrogenase (AlDH), thereby producing physiological effects that deter further drinking by alcoholics.

The absorption of calcium carbimide following oral administration is extremely rapid, causing nausea, headache and vomiting. In an attempt to reduce the rate of absorption, calcium carbimide is formulated as a slow release tablet, and to prevent its decomposition to ammonia, it is prepared in the citrated form (1 part drug to 2 parts citric acid). In the gastric juices, calcium carbimide is hydrolyzed to carbimide (cyanamide, $H_2NCN$) which is rapidly absorbed into the portal circulation. Data from animal experiments indicate that the drug is rapidly absorbed, metabolized and eliminated, and in view of the rapid onset and short duration of the calcium carbimide-ethanol reaction (CER), it is likely that absorption, metabolism and elimination are also rapid in humans. Cyanamide itself does not inhibit AlDH, but must be enzymatically activated by catalase to an as-yet unidentified active metabolite.

Disulfiram continues to be widely used in alcoholism treatment; however, there has been concern that its repeated use may induce toxicity. The use of calcium carbimide is not approved in the United States. In Canada and other countries, calcium carbimide has not been widely used because of its short duration of activity, which lasts approximately 24 hours. This is due to its facile conversion in vivo to an acetylated derivative, viz. acetylcyanamide (AC), which is rapidly excreted in the urine. At least 94% of the administered cyanamide is eliminated within 6 hours via this route by the rat. Like cyanamide, AC is devoid of AlDH inhibitory activity in vitro.

Therefore a continuing need exists for alcohol sensitizing and deterrent drugs which can substantially elevate blood acetaldehyde levels in the presence of ethanol for a prolonged period following oral administration.

SUMMARY OF THE INVENTION

The present invention is directed to a series of cyanamide derivatives of general structure RCONHCN, which are prepared by substituting the amino nitrogen atom of cyanamide with lipophilic acyl and N-substituted-(α-aminoacyl) groups. In vivo, the enzymatic cleavage of these acyl groups (RCO) results in the gradual release of cyanamide. Thus, the preferred compounds of the present invention are superior to cyanamide or its salts with respect to (a) the elevation of blood acetaldehyde levels after ethanol administration, and/or (b) the duration of action. Therefore, the present invention is also directed to a method of deterring ethanol intake comprising raising the blood acetaldehyde level of a human following ethanol intake by administering an effective amount of one of the compounds of the present invention.

The present alcohol sensitizing composition includes compounds of the formula I:

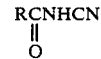

$$\underset{\underset{O}{\|}}{RCNHCN} \qquad I$$

wherein R is $C_3$–$C_{30}$(alkyl), aryl, or cycloalkyl group; preferably a $C_{12}$–$C_{22}$ alkyl or a $C_5$–$C_{12}$ cycloalkyl group; said alkyl group comprising from 0–3 double bonds. Therefore, the RCO acyl group is preferably derived from a saturated or unsaturated fatty acid such as an alkanoic, alkenoic, dienoic or trienoic acid. Such acids include lauric, oleic, palmitic, linoleic, linolenic, stearic, eleastearic, palmitic, palmitoleic, petroselenic, vaccenic, erucic acid and the like. Other preferred R groups include propyl, butyl and branched alkyl groups such as t-butyl (from pivalic acid) or cycloalkyl groups comprising 1–4 rings, such as cyclohexyl, cyclopropylmethyl, norbornyl, cyclopentyl, adamantyl and the like. Preferred aryl groups include phenyl, benzyl, benzyloxy, tolyl and variously-substituted aryl groups including heteroaryl groups.

The R group of the compounds of formula I may also be represented by the formula $(R_2)NHCH(R_1)$ wherein $R_1$ is H, benzyl, or a $C_3$–$C_6$ alkyl group, and $R_2$ is benzoyl, (N-carbobenzyloxy) or (L-pyroglutamyl). Thus, the RCO moiety of the compounds of formula I can be derived from an (N-protected)-α-amino acid or from and N-[N-protected)(α-amino)acyl]-α-amino acid. Preferably $R_1$ is benzyl or i-butyl. Preferred RCO groups of this type include hippuryl ($C_6H_5CONHCH_2CO$), N-benzoyl-L-leucyl, (N-carbobenzyloxy) glycyl-L-leucyl, (L-pyroglutamyl)-L-Leucyl and (L-pyroglutamyl)-L-phenylalanyl. RCO may also be the moiety N-carbobenzyloxy-L-pyroglutamyl.

Especially preferred acylated cyanamides of the present invention, due to their ability to rapidly elevate blood acetaldehyde levels to alcohol-deterrent levels and/or their ability to elevate blood acetaldehyde levels for a prolonged period, include n-butyrylcyanamide, palmitoylcyanamide ($R=C_{15}$-n-alkyl), stearoylcyanamide ($R=C_{17}$-n-alkyl), N-benzoyl-L-leucyl-cyanamide, hippuryl cyanamide, N-carbobenzyloxy-glycyl-L-leucylcyanamide and L-pyroglutamyl-L-phenylalanylcyanamide, and the pharmaceutically acceptable salts thereof.

The present invention also is directed to a method of discouraging ethanol intake and abuse by a human comprising raising the blood acetaldehyde level of a human following ethanol intake by administering an effective amount of one of the compounds of the present invention. Other compounds which can be used in this method are acetylcyanamide and propionylcyanamide. Therefore, the present invention can also include the pharmaceutically-acceptable salts of these acylated cyanamides, together with a pharmaceutically-acceptable carrier for administration in an effective non-toxic dose form. Pharmaceutically-acceptable amide salts may include metal salts, such as the alkali and alkaline earth metal salts, e.g., sodium, potassium, lithium and the like.

These physiologically acceptable salts are prepared by methods known in the art. Metal salts can be prepared by reacting a controlled amount of a metal hydroxide with the free cyanamide. Examples of metal salts which can be prepared in this way are salts containing Li, Na, K, Ca, Mg, Zn, Mn and Ba. A less soluble metal salt can be precipitated from a solution of a more soluble salt by addition of a suitable metal compound. Thus for examples, Zn, Mg and Mn salts can be prepared from the corresponding sodium salts. The metal ions of a given metal salt can be exchanged by hydrogen ions, other metal ions, ammonium ion, guanidinium ion and ammonium and guanidinium ions substituted by one or more organic radicals by using a suitable cation exchanger.

Figure 1:
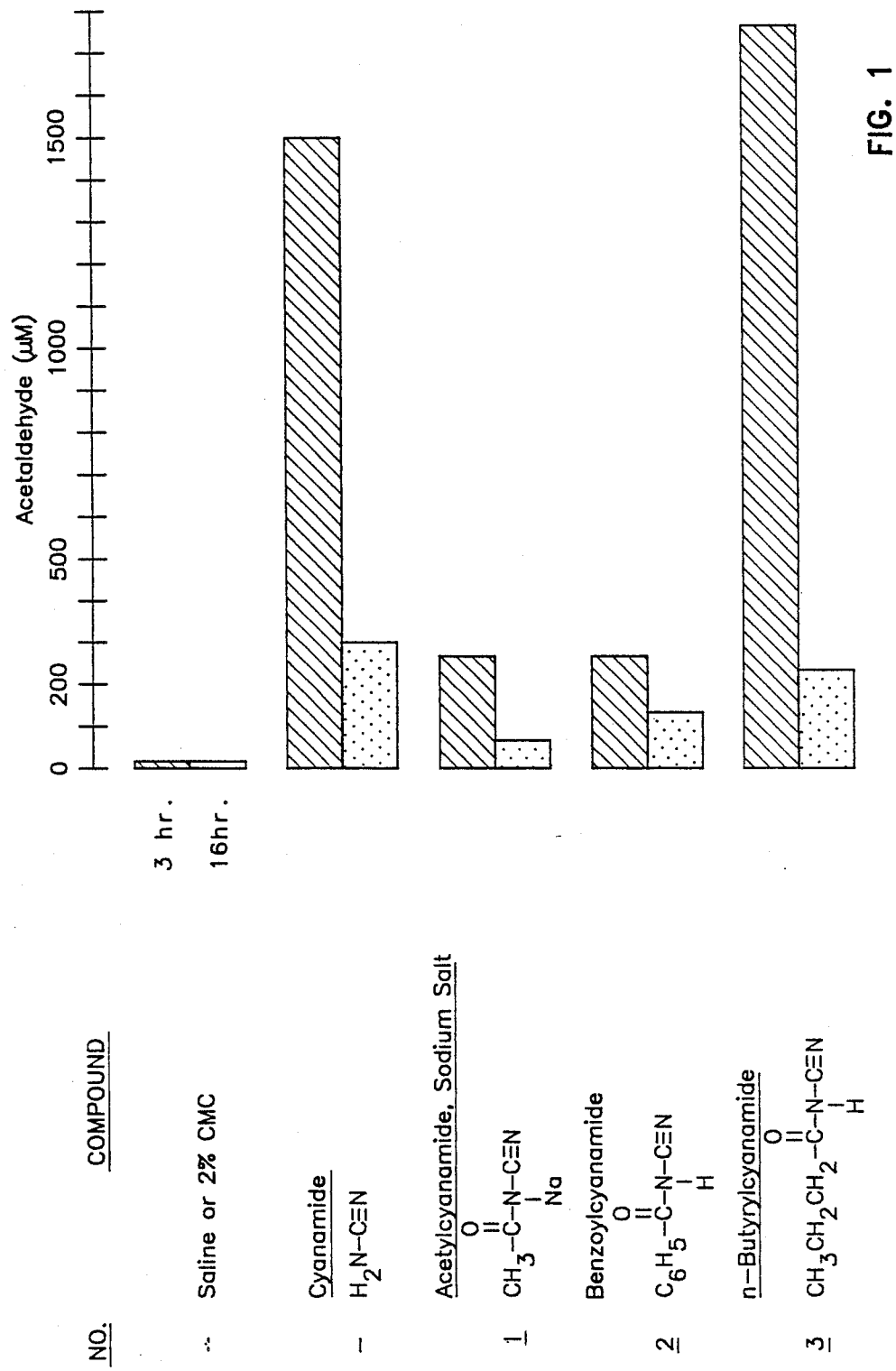
FIGS. 1–4 graphically depict the effectiveness of certain of the compositions of the invention in elevating blood acetaldehyde (AcH) following ethanol administration in rats.
Figure 2:
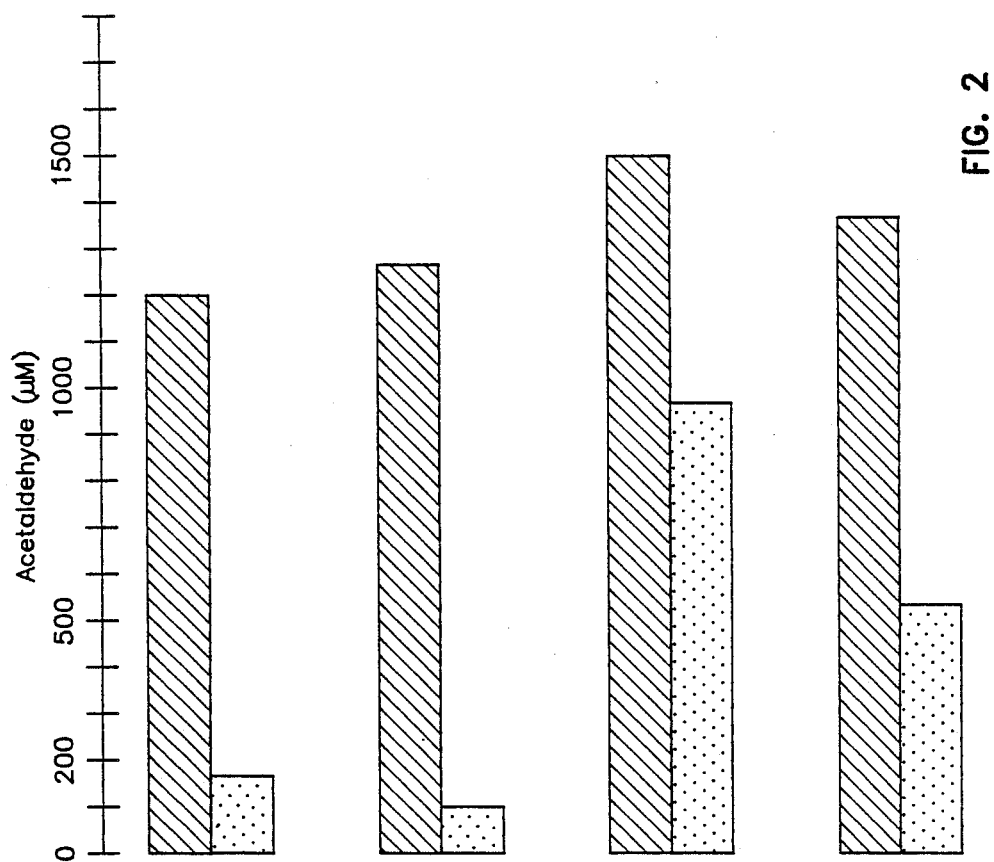
Figure 3:
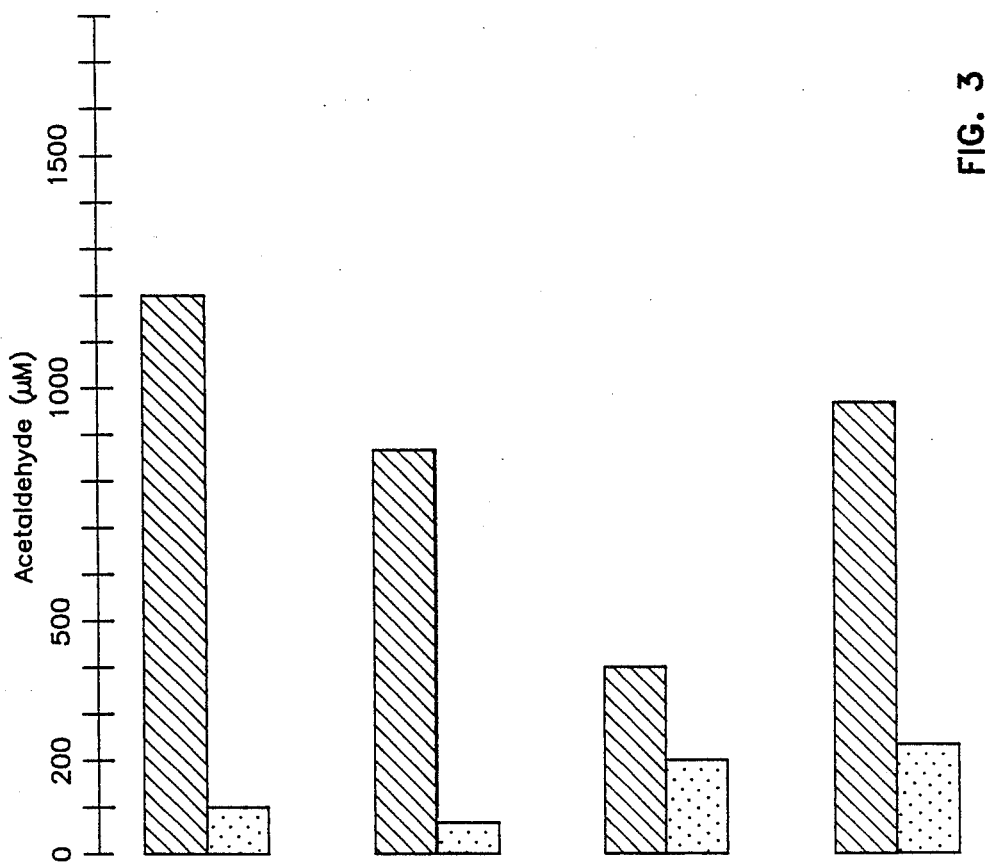
Figure 4:
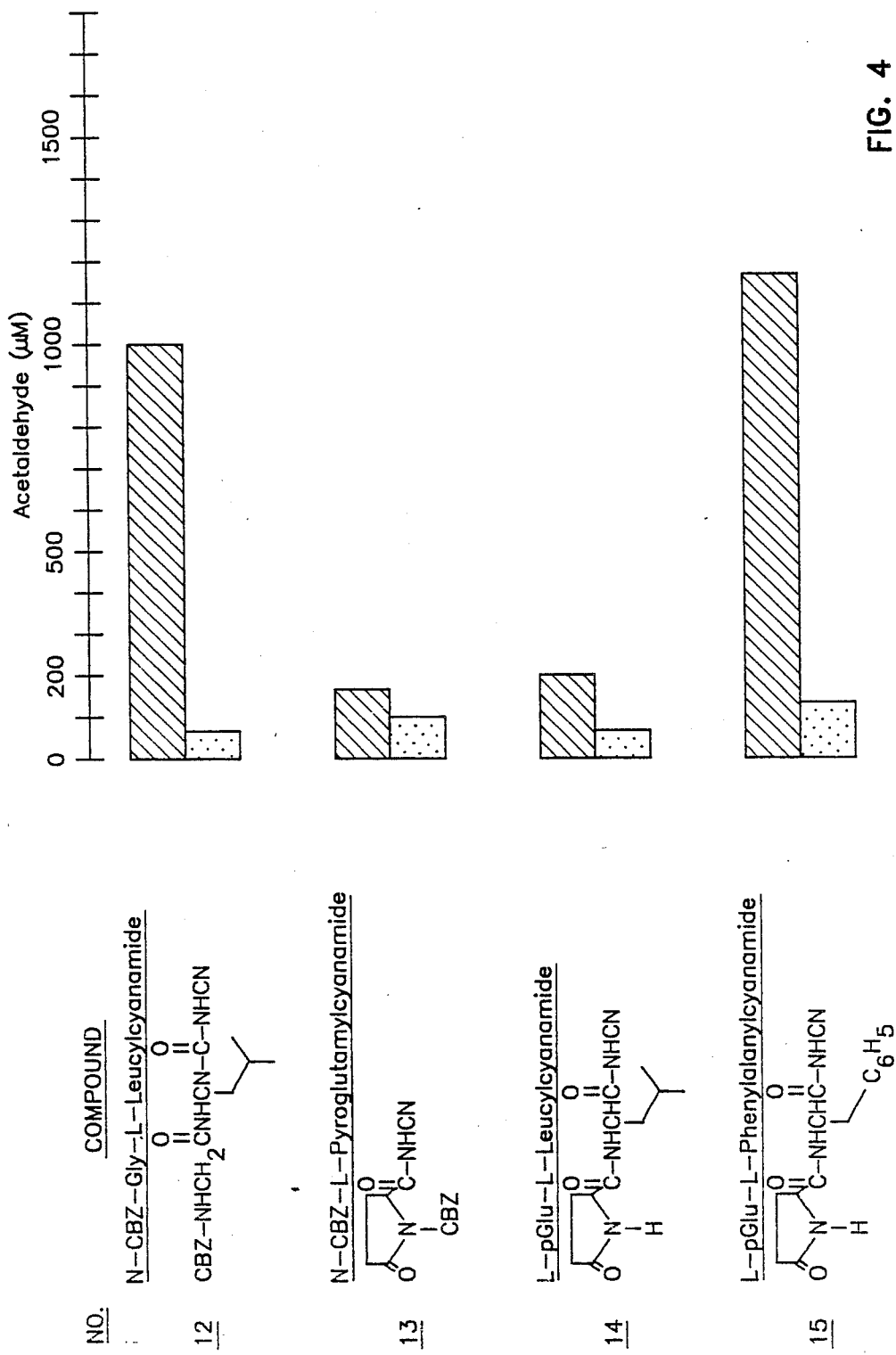

The following abbreviations appear in the figures: CBZ=carbobenzyloxy; Gly=glycyl; and pGlu=pyroglutamyl.

DETAILED DESCRIPTION OF THE INVENTION

Acylated cyanamides of the general fomula I, wherein R is a $C_3$–$C_{30}$, aryl (e.g. phenyl) or cycloalkyl group can be readily prepared by acylation of an alkali metal cyanamide salt, such as monosodium cyanamide, with the acid chloride RCOCl. The reaction can be carried out at about $-5°$ C. to $30°$ C. in an inert solvent such as tetrahydrofuran for about 10–80 hours. Following partition of the reaction mixture between water and an organic solvent such as ethyl acetate, the aqueous phase containing the sodium salt of the product is acidified with dilute mineral acid, extracted with an organic solvent such as chloroform and the solvent removed to yield the crude product. The product can be purified by crystallization and/or thin layer- or column-chromatographic techniques. Variations of this procedure are set forth in the Examples hereinbelow.

In the case where the desired acid chloride is not commercially available, it can be prepared from the corresponding carboxylic acid by reaction of the acid with thionyl chloride in the presence of triethyl amine or with $(COCl)_2$ or $PCl_3$. See, Compendium of Organic Synthetic Methods, I. T. Harrison et al., eds., Wiley-Interscience, Pub., New York (1971) at pages 22–24, the disclosure of which is incorporated by reference herein.

Acylated cyanamides of formula I wherein R is $R_2CONHCH(R_1)$—, wherein $R_1$ and $R_2$ are defined as hereinabove or wherein RCO is (N-carbobenzyloxy-L-pyroglutamyl-) can be derived from the corresponding (N-protected)-α-(amino)acid or from the corresponding N-[(N-protected)-(α-amino)acyl]-α-amino acid (a protected dipeptide) by conversion of the free $CO_2H$ mostly to the corresponding activated N-hydroxysuccinimide ester by reaction with N-hydroxysuccinimide in the presence of dicyclohexylcarbodiimide (DCC). The activated ester readily reacts with cyanamide in the presence of an alkali metal hydroxide to yield the protected, acylated cyanamide of formula $R_2CONHCH(R_1)CONHCN$ following acidification. N-protected-α-amino acids can also be converted to the corresponding activated N-hydroxysuccinimide esters and reacted with a second α-amino (benzyl) ester to provide the dipeptide starting materials employed in the present invention, $(R_2CONHCH(R_1)CO_2H)$, following removal of the benzyl ester by hydrogenolysis. See L. F. Fieser et al., Reagents for Organic Synthesis, John Wiley and Sons, Inc., New York (1967) at pages 485 and 487, the disclosure of which is incorporated by reference herein.

Other activated intermediates can be employed, such as the mixed anhydride i-BuOCOCOR which is formed by reaction of the amino acid ($RCO_2H$) with i-BuOCOCl in the presence of (N-methyl)morpholine. Amino protecting groups are selected from those which are base stable, such as the t-butoxycarbonyl and carbobenzyloxy groups Pyroglutamic acid is a self-protected cyclic amide of glutamic acid.

In clinical practice, acylated cyanamides or the salts thereof will normally be administered orally in the form of a pharmaceutical unit dosage form comprising the active ingredient in combination with a pharmaceutically-acceptable carrier which may be a solid, semi-solid or liquid diluent or an ingestible capsule. A unit dosage of the compound or its salt may also be administered without a carrier material. As examples of pharmaceutical preparations may be mentioned tablets, capsules, aqueous solutions, suspensions, liposomes, and other slow-release formulations. Usually the active substance will comprise between about 0.05% and 99%, or between 0.1% and 95% by weight of the unit dosage form, for example, between about 0.1% and 50% of preparations intended for oral administration.

The amount of the acylated cyanamide administered and the frequency of administration to a given human patient will depend upon a variety of variables related to the patient's psychological profile and physical condition. For evaluations of these factors, see J. E. Peachey, A Review of the Clinical Use of Disulfiram and Calcium Carbimide in Alcoholism Treatment, J. Clinical Psychopharmacology, 1, 368 (1981), J. F. Brien et al., Europ. J. Clin. Pharmacol., 14, 133 (1978), and Physicians' Desk Reference, Charles E. Baker, Jr., Pub., Medical Economics Co., Oradell, N.J. (34th ed., 1980) at page 591–592. Generally, although the initial unit dose of the present compounds may be similar to that administered in the case of calcium cyanamide, e.g., 0.5–1.0 mg/kg, the unit dose preferably need not be readministered for 24–96 hours, versus about 8–12 hours in the case of calcium cyanamide.

The invention will be further described by reference to the following detailed examples I. Synthesis of Acylated Cyanamides.

Example 1. Sodium Acetylcyanamide (1)

Sodium acetylcyanamide was prepared by the acetylation of sodium cyanamide (Fluka Chemical Corp., Hauppauge, N.Y.) by the method of F. N. Shirota et al., Drug Metab. Disp., 12, 337 (1984), the disclosure of which is incorporated by reference herein.

Example 2. Benzoylcyanamide (2)

Benzoylcyanamide was prepared by the addition of benzoyl chloride (6.33 g, 0.045 mol) in 100 ml of diethyl ether to a suspension of monosodium cyanamide (5.76 g, 0.090 mol) in 100 ml of ether at 4° C. The reaction was stirred overnight at room temperature and the pale yellow solid which formed was collected and dissolved in water. On acidification of the solution to pH 1, a precipitate formed which was collected and recrystallized from ethyl acetate (EtOAc)/petroleum ether (30°–60° C.) to give 2 (5.89 g, 89.7% yield), mp 140°–142° C. [reported mp 139°–140° C.]. Anal. Calcd for $C_8H_6H_2O$: C, 65.75; H, 4.11; N, 19.18. Found: C, 65.79; H, 4.35; N, 19.04.

Example 3. Pivaloylcyanamide (3)

Pivaloyl chloride (2.41 g, 2.46 ml, 0.020 mol) in 50 ml of tetrahydrofuran (THF) was added drop-wise to a suspension of sodium cyanamide (3.84 g, 0.060 mol) in 100 ml of THF at ice bath temperature with stirring. The reaction was allowed to proceed at 25° C. overnight. The reaction mixture was then extracted with ethyl acetate (2×50 ml). The aqueous layer (pH 10.5) was separated, acidified to pH 1.5 with 10% aqueous HCl, and extracted with chloroform (3×50 ml). The choloroform extract was dried over anhydrous sodium sulfate, filtered, and the filtrate was evaporated in vacuo to give 2.15 g (85.2% yield) of crude product. This was crystallized from ethyl acetate and petroleum ether (b.p. range 30°–60° C.) to yield 1.4 g of white crystalline 3, mp 112°–118° C. TLC: $R_f$=0.56 in ethyl acetate/petroleum ether/ acetic acid (AcOH) (50:100:1), detected by orange color with ferricyanide spray reagent; IR (Nujol, $cm^{-1}$) 3180 (NH), 2240 (C≡N), 1730 (C=O); NMR (Silanor C, δ from TMS) 1.26 (s, $(CH_3)_3C$—). Anal. Calcd for $C_6H_{10}N_2O$: C, 57.12; H, 7.99; N, 22.20. Found: C, 56.98; H, 7.93; N, 22.12.

Example 4. 1-Adamantanecarbonyl Cyanamide (1-Adamantoylcyanamide) (4)

1-Adamantanecarbonyl chloride (1.99 g, 0.010 mol) in 50 ml of THF was added drop-wise to a suspension of sodium cyanamide (1.92 g, 0.030 mol) in 100 ml of THF with stirring at ice bath temperature. The reaction was allowed to proceed at 25° C. for 15 hours. The reaction mixture was then extracted with ethyl acetate (100 ml). The separated aqueous portion (pH 10.5) was acidified to pH 1.5 with 10% HCl and extracted with ethyl acetate (3×60 ml). The ethyl acetate extract was dried over anhydrous sodium sulfate, filtered, and the filtrate was evaporated in vacuo to dryness. The resulting white solid residue was triturated in a minimal amount of distilled water, filtered, and air-dried to give 1.74 g (85.2% yield) of crude 4 as white solid. This was recrystallized from ethyl acetate and petroleum ether to give 0.55 g (crop 1) of white crystalline powder. The filtrate was concentrated when further crystallization occurred to give 0.49 g (crop 2) of additional product giving a total yield of 50.9%, mp 168°–170° C. TLC: $R_f$=0.58 in EtOAc/petroleum ether/AcOH (50:100:1), detected by UV quenching (weak) and reddish orange color with ferricyanide spray reagent; IR (Nujol, $cm^{-1}$) 3210 (NH), 2230 (C≡N), 1710 (C=O); NMR (Silanor C, δ from TMS) 1.62-2.2 (m, aliphatic CH's). Anal. Calcd for $C_{12}H_{16}N_2O$: C, 70.56; H, 7.90; N, 13.71. Found: C, 70.59; H, 8.04; N, 13.66.

Example 5. n-Butyrylcyanamide (5)

n-Butyryl chloride (3.2 g, 3.12 ml, 0.030 mol) in 50 ml of freshly distilled dry THF was added drop-wise to a suspension of sodium cyanamide (5.76 g, 0.090 mol) in 100 ml of freshly distilled dry THF at ice bath temperature. The reaction was allowed to proceed at room temperature for 24 hours and then the mixture evaporated to dryness in vacuo. The resulting yellow solid residue was dissolved in distilled water (50 ml) and the alkaline solution was adjusted to pH 6.5 with 10% HCl. The mixture was then extracted with ethyl acetate (2×50 ml). The aqueous portion (pH 7.8 was acidified to pH 1.5 with 10% HCl and extracted with methylene chloride (3×30 ml). The organic layer was separated, dried over anhydrous sodium sulfate and evaporated in vacuo to give 3.33 g (99.0% yield) of the crude product as a pale yellow liquid. A portion of the crude 5 (2.00 g, 0.0178 mol) was applied to a dry silica gel column (22×2.5 cm, 230-400 mesh, EM reagent) in EtOAc/petroleum ether (1:3) and eluted with the same solvent by flash chromatography at 15 psi. A total of 32×20 ml fractions were collected. The fractions containing the desired compound were pooled and evaporated in vacuo to give 1.77 g (total yield, 87.6%) of pure 5 as a clear colorless liquid. This compound decomposes on standing even at 5° C. after prolonged periods. TLC: $R_f$=0.6 in EtOAC/petroleum ether/AcOH (50:100:1), detected by UV quenching and orange color with ferricyanide spray reagent; IR (neat, $cm^{-1}$) 3100-3250 (NH), 2860-2960 (alkyl), 2260 (C≡N), 1725 (C=O); NMR (Silanor C, δ from TMS) 8.2-8.5 (broad, NH), 2.3-2.6 (t, —$CH_2$—$CH_2$—C=O), 1.5-1.9 (sextet, $CH_3$—$CH_2$—$CH_2$—), 0.8-1.1 (t, $CH_3$—$CH_2$—); CI-MS ($NH_3$: positive) m/z (rel. intensity) 147 (12.6, [(M+1)+$2NH_3$]), 130 (100.0) [(M+1)+$NH_3$], 105 (5.2) [(M+1)+$2NH_3$—$H_2NCN$]; CI-MS ($NH_3$: negative) m/z (rel. intensity) 111 (100.0) [M−1], 68 (2.0) [(M−1)—$CH_3CH_2CH_2$], 41 (16.7) [(M−1)—$CH_3CH_2CH$=C=O ].

Example 6. Palmitoylcyanamide (6)

A solution of palmitoyl chloride (5.5 g, 0.020 mol) in 50 ml of freshly distilled dry THF was added drop-wise to a suspension of sodium cyanamide (3.84 g. 0.060 mol) in 150 ml of freshly distilled dry THF at ice bath temperature. After the addition, the ice bath was removed and the reaction was allowed to proceed at 25° C. for 43 hours. The solids that formed were filtered to yield 8.48 g of waxy solid residue. The residue was ground to a fine powder and stirred in 150 ml of distilled water at ice bath temperature. The resulting soapy suspension (pH 11) was acidified to pH 2 with 10% HCl, then filtered and air-dried to give 5.4 g (96.3% yield) of crude 6 as a white solid. This was dissolved in warm THF and the mixture filtered. The filtrate was concentrated in vacuo until the solution became slightly turbid. This material was crystallized from THF/petroleum ether to yield 3.6 g (crop 1) of white powder. The filtrate was concentrated and crystallized in the same fashion to yield additional 0.6 g (crop 2) of white powder (74.8% total yield), mp 62°–65° C. TLC: $R_f$=0.68 in ethyl acetate/petroleum ether/glacial acetic acid (10:20:1); IR (Nujol, $cm^{-1}$) 3230 (NH), 2250 (C≡N), 1740 (C=O); NMR (Silanor C, δ from TMS) 1.3-1.6 (t, —$CH_2$—$CH_2$—C=O), 1-1.8 (m, —$(CH_2)_{13}$—), 0.8-1 (t, $CH_3$—$CH_2$—); Anal. Calcd for $C_{17}H_{32}N_2O$: C, 72.81; H, 11.50; N, 9.99. Found: C, 72.69; H, 11.65; N, 9.68.

Example 7. Stearoylcyanamide (7)

Stearoyl chloride (3.03 g, 0.010 mol) in 50 ml of freshly distilled dry THF was added drop-wise to a suspension of sodium cyanamide (1.92 g, 0.030 mol) in 100 ml of freshly distilled dry THF with vigorous stirring. The reaction was allowed to proceed at 25° C. for 63 hours. The solids which formed were collected by filtration and the solid cake was suspended in 200 ml of distilled water. The resulting soapy suspension (pH 10.5) was acidified to pH 1.5 with 10% HCl, filtered, and air-dried to give 2.85 g (92.4% yield) of crude 7. This was dissolved in THF and the solution decolorized with activated charcoal. The filtrate was concentrated until the solution became turbid. Addition of petroleum ether gave 2.29 g (crop 1) of white waxy 7. The filtrate was concentrated and petroleum ether added to give 0.28 g (crop 2) of additional product giving a total yield of 83.3%, mp 74°–75° C. TLC: $R_f$=0.69 in EtOAc/petroleum ether/AcOH (50:100:1), detected by UV quenching (weak) and no color reaction with ferricyanide spray reagent; IR (Nujol, cm$^{-1}$) 3210 (NH), 2250 (C≡N), 1735 (C=O); NMR (Silanor C, δ from TMS) 2.3–2.6 (t, —CH$_2$—CH$_2$—C=O), 1.0–1.8 (fused s, (CH$_2$)$_{14}$), 0.8–0.9 (t, CH$_3$—CH$_2$—); Anal. Calcd for C$_{19}$H$_{36}$N$_2$O: C, 73.97; H, 11.76; N, 9.08. Found: C, 73.88; H, 11.50; N, 9.09.

Example 8. N-Carbobenzoxycyanamide, Sodium Salt (8)

To a stirred solution of cyanamide (6.3 g, 0.15 mol) in 60 ml of distilled water, were added carbobenzoxy chloride (8.5 g, 0.050 mol) and 10% NaOH (40 ml, 0.10 mol) drop-wise via separate funnels at ice bath temperature. The reaction was allowed to proceed at this temperature for 3 hours. The reaction mixture (pH 10.1) was extracted with ethyl acetate (2×50 ml) and diethyl ether (2×50 ml), then the aqueous layer was acidified with 10% HCl to pH 1.5 and extraction with diethyl ether (4×50 ml). The ether extract was dried over anhydrous sodium sulfate and filtered. The filtrate was evaporated in vacuo to give a pale pink clear liquid. The liquid was dissolved in 50 ml of methanol at ice bath temperature. The methanolic solution (pH 1.8) was titrated with 5% methanolic NaOH to pH 5.9, the solution filtered, and the filtrate was evaporated in vacuo to near dryness to give a pale yellow liquid. Diethyl ether (100 ml) was added to the liquid with occasional shaking. After some scratching with a glass rod, a white solid cake formed. The collected white solid was washed with diethyl ether to give 5.17 g (52.2% yield) of pure 8 as a white powder, mp 216°–217° C. TLC: $R_f$=0.56 in CH$_2$Cl$_2$/CH$_3$OH (5:1); detected by UV quenching and orange color with ferricyanide spray reagent; IR (Nujol, cm$^{-1}$) 3100–3040 (C$_6$H$_5$), 2150 (—N=C=N—Na), 1640 (—O$_2$C—N); NMR (Silanor D$_2$O/DSS, δ from DSS), 7.38 (s, C$_6$H$_5$), 5.03 (s, C$_6$H$_5$—CH$_2$—O—). Anal. Calcd for C$_9$H$_6$N$_2$O$_2$. Na: C, 54.55; H, 3.56; N, 14.14. Found: C, 54.57; H, 3.79; N, 14.26.

Example 9. N-Carbobenzoxyglycine N-Hydroxysuccinimide Ester

Acetonitrile (100 ml) was added to a reaction vessel containing N-carbobenzoxyglycine (4.18 g, 0.020 mol), dicyclohexyl carbodiimide (4.13 g, 0.020 mol), and N-hydroxysuccinimide (2.3 g, 0.020 mol) were stirred in 100 ml of acetonitrile at ice bath temperature for 5 hours. The reaction mixture was filtered to remove 4.12 g of white crystalline dicyclohexyl urea (DCU) as by-product. The filtrate was evaporated in vacuo to give a semi-solid residue which was recrystallized from chloroform/petroleum ether (bp range: 60°–70° C.) to give 4.99 g (81.5% yield) of white, crystalline N-carbobenzoxyglycine N-hydroxysuccinimide ester, mp 111° C. IR (Nujol, cm$^{-1}$) 3300 (NH), 3020 and 3060 (C$_6$H$_5$), 1820, 1780, 1740, and 1690 (C=O). Anal. Calcd for C$_{14}$H$_{14}$N$_2$O$_6$: C, 54.90; H, 4.61; N, 9.15. Found: C, 54.15; H, 4.63; N, 8.75.

Example 10. N-Carbobenzoxyglycylcyanamide (9)

A solution of N-carbobenzoxyglycine N-hydroxysuccinimide ester (1.53 g, 5.0 mol) in 50 ml of THF and 10% NaOH (4 ml, 0.4 g, 0.010 mol) were added drop-wise, simultaneously via separate channels, to a reaction vessel containing cyanamide (0.63 g, 0.015 mol) in 100 ml of distilled water, with stirring at ice bath temperature. The reaction was allowed to proceed overnight at room temperature. The reaction mixture (pH 9.5) was extracted with ethyl acetate (2×50 ml). The ether was dried over anhydrous sodium sulfate, filtered, and the filtrate was evaporated in vacuo to give 1.0 g (86% yield) of crude product as a white solid residue. It was recrystallized from THF/petroleum ether (bp range: 60°–70° C.) to give 0.50 g (43% yield) of white, crystalline 9, mp 198° C. dec. IR (Nujol, cm$^{-1}$) 3300, 3100 (NH), 2250 (C N), 1725 and 1680 (C=O). Anal. Calcd for C$_{11}$H$_{11}$N$_3$O$_3$: C, 56.65; H, 4.75; N, 18.02. Found: C, 56.77; H, 4.53; N, 17.95.

Example 11. N-Benzoylglycylcyanamide (Hippurylcyanamide) (10)

Hippuric acid (3.58 g, 0.020 mol), DCC (4.13 g, 0.020 mol), and N-hydroxysuccinimide (2.3 g, 0.020 mol) were stirred in 100 ml of acetonitrile at ice bath temperature for 2 hours. The reaction mixture was filtered to remove the bulk of by-product DCU. The filtrate was evaporated in vacuo to dryness, the residue was redissolved in THF and the mixture was filtered to remove any residual DCU. The filtrate (70 ml) was added drop-wise to a solution of sodium cyanamide (3.84 g, 0.060 mol) in 100 ml of distilled water with vigorous stirring at ice bath temperature. The reaction was allowed to proceed at room temperature overnight. The reaction mixture (pH 11) was extracted with ethyl acetate (2×60 ml) and the separated aqueous layer was acidified to pH 1.5 with 10% HCl. The resulting solid suspension was filtered to give 2.28 g (56.1% yield) of white crystalline 10. It was recrystallized from THF/acetonitrile/petroleum ether to yield 0.78 g (crop 1) of white crystalline product. The filtrate was concentrated to yield 0.9 g (crop 2) of additional crystals. Mp dec. >155° C. (turns to brown oil at 160° C.); TLC: $R_f$=0.36 in EtOAc/AcOH (100:1), detected by UV quenching and orange color with ferricyanide spray reagent; IR (Nujol, cm$^{-1}$) 3400 (NH), 3080 (C$_6$H$_5$), 2220 (C≡N), 1710 and 1620 (C=O); NMR (Silanor C and DMSO (1:1), δ from TMS) 8.2–8.4 (broad, NH); 7.3–8.0 (m, C$_6$H—), 4.1–4.2 (d, —NH—CH$_2$—CO) Anal. Calcd for C$_{10}$H$_9$N$_3$O$_2$: C, 59.11; H, 4.46; N, 20.68. Found: C, 59.26; H, 4.46; N, 20.84 (crop 1) and C, 59.03; H, 4.20; N, 20.80 (crop 2).

Example 12. N-Benzoyl-L-leucine

Benzoyl chloride (4.22 g, 0.030 mol) and 10% NaOH (12 ml, 0.030 mol) were added separately with vigorous stirring to a solution of L-leucine (3.94 g, 0.030 mol) in 150 ml of distilled water at ice bath temperature. The reaction was allowed to proceed at this temperature until the reaction mixture became clear (30 minutes); it was then extracted with ethyl acetate (2×100 ml). The aqueous layer was separated, acidified to pH 2 with 10% HCl, and extracted with ethyl acetate (3×50 ml). The ethyl acetate extract was dried over anhydrous sodium sulfate. After filtration, the filtrate was evaporated in vacuo to yield quantitative amount of N-benzoyl-L-leucine as a semi-solid which was used directly for the following step.

Example 13. N-Benzoyl-L-leucylcyanamide (11)

DCC (2.41 g, 0.0117 mol) and N-hydroxysuccinimide (1.35 g, 0.0117 mol) were added to a solution of N-benzoyl-L-leucine (2.75 g, 0.0117 mol) in 100 ml of acetonitrile at ice bath temperature. The reaction was allowed to proceed at this temperature for 2 hours. The reaction mixture was filtered to remove the bulk of the DCU and the filtrate was evaporated in vacuo to dryness. The resulting semi-solid residue was redissolved in THF and the mixture filtered to remove any residual DCU. The filtrate was evaporated in vacuo to give crude N-benzoyl-L-leucine N-hydroxysuccinimide ester as a foamy residue IR (neat, cm$^{-1}$) 3340 (NH), 3060 ($C_6H_5$), 1820, 1790, 1740 and 1650 (C=O); NMR (Silanor C, δ from TMS) 7.3–7.9 (m, $C_6H_5$), 5.1–5.3 (m, —NH—CH—C=O), 2.8 (s, cycl. —$CH_2$—$CH_2$—), 1.6–2.2 (m, C$\underline{H}$—$CH_2$—), 0.9–1.1 (d, ($C\underline{H}_3$)$_3$C$\underline{H}$). This was dissolved in 100 ml of THF and added drop-wise to a solution of sodium cyanamide (1.50 g, 0.0234 mol) in 100 ml of distilled water at ice bath temperature. The reaction was allowed to proceed at room temperature for 24 hours. The reaction mixture was then concentrated in vacuo to half its original volume and filtered. The filtrate (pH 9) was extracted with ethyl acetate (2×50 ml). The aqueous layer was separated, acidified to pH 1.5 with 10% HCl, and extracted with methylene chloride (3×50 ml). The methylene chloride extract was dried over anhydrous sodium sulfate and filtered. The filtrate was evaporated in vacuo to give 2.80 g (92.4% yield) of crude product as a tacky white solid. This was triturated with diethyl ether and collected to give 1.30 g (42.9% yield of white powdery 11, mp 136°–137° C. $[\alpha]_D^{23}$ +0.7° (c 1.0, $CH_3OH$); TLC: $R_f$=0.93 in EtOAc/petroleum ether/THF/$CH_2Cl_2$/AcOH (50:50:10:50:4) and 0.24 in EtOAc/petroleum ether/AcOH (50:100:1), detected by UV quenching and orange color with ferricyanide spray reagent; IR (Nujol, cm$^{-1}$) 3300, 3100 (NH), 2230 (C≡N), 1750 and 1630 (C=O); NMR (Silanor-DMSO, δ from TMS) 7.4–8.0 (d, $C_6H_5$—), 4.2–4.6 (m, —NH—CH—C=O), 1.4–1.9 (m, C$\underline{H}$—$CH_2$—), 0.8–1.1 (d, ($C\underline{H}_3$)$_2$CH—). Anal. Calcd for $C_{14}H_{17}N_3O_2$: C, 64.85; H, 6.61; N, 16.20. Found C, 64.62; H, 6.73; N, 15.93.

Example 14. N-Cbz-glycyl-L-leucylcyanamide (12)

N-Cbz-glycyl-L-leucine (4.84 g, 0.015 mol) was allowed to react with DCC (3.09 g, 0.015 mol) and N-hydroxysuccinimide (1.73 g, 0.015 mol) in 50 ml of THF at ice bath temperature for 2.5 hours. The reaction mixture was filtered and the light brown filtrate (50 ml) was added to a solution of sodium cyanamide (2.88 g, 0.045 mol) in 30 ml of distilled water with stirring at ice bath temperature. The reaction was allowed to proceed at room temperature for 24 hours. The reaction mixture was concentrated in vacuo to half its original volume and filtered. The filtrate (pH 9) was acidified to pH 2.5 with 10% HCl and extracted with methylene chloride (4×50 ml). The combined methylene chloride extract was dried over anhydrous sodium sulfate, filtered, and the filtrate was evaporated in vacuo to give 4.86 g (93.5% yield) of crude 10 as a thick semi-solid residue. The residue was dissolved in methylene chloride and the solution washed with 5% citric acid. The organic layer was separated, dried over anhydrous sodium sulfate, and decolorized with activated charcoal. After removal of the charcoal by filtration, the filtrate was evaporated in vacuo to give 4.10 g (78.9% yield) of white glassy 10, mp 50°–55° C. $[\alpha]_D^{23}$ −34.0° (c 1.0, MeOH); TLC: $R_f$=0.54 in $CH_2Cl_2$/MeOH/AcOH (90:10:5), detected by UV quenching and orange color with ferricyanide spray reagent; IR (Nujol, cm$^{-1}$) 3300 (NH), 3060 ($C_6H_5$), 2260 (C≡N), 1650–1730 (C=O); NMR (Silanor C, δ from TMS) 7.35 (s, $C_6H_5$—), 5.7–6.1 (NH), 5.1 (s, —O—$CH_2$), 4.3–4.7 (m, —NH—C$\underline{H}$—CO), 3.8–4.0 (fused s, —NH—$CH_2$—CO), 1.4–1.8 (m, —$CH_2$—CH=), 0.8–1.0 (fused d, ($CH_3$)CH—) Anal. Calcd for $C_{17}H_{22}N_4O_4$: C, 58.95; H, 6.40; N, 16.17. Found: C, 58.90; H, 6.55; N, 15.93.

Example 15. N-Cbz-L-pyroglutamic Acid N-Hydroxysuccinimide Ester

DCC (2.27 g, 0.011 mol) was added to a solution of Cbz-L-pyroglutamic acid (2.63 g, 0.010 mol) and N-hydroxysuccinimide (1.15 g, 0.010 mol) in 50 ml of THF at 0° C., and the mixture was stirred at room temperature for 15 hours. The reaction mixture was filtered and the filtrate was evaporated to give 3.50 g (97.1% yield) of crude product as a thick liquid which flocculated on addition of petroleum ether. The precipitate was crystallized from isopropyl alcohol to give 2.15 g (crop 1) of white crystals. The filtrate was concentrated and crystallized in the same manner to give 0.71 g (crop 2) giving a total yield of 79.4%. Mp 132°–134° C. [reported mp 131°–133° C.]; TLC: $R_f$=0.77 in EtOAc/AcOH (100:1), detected by UV quenching; IR (Nujol, cm$^{-1}$) 3050 ($C_6H_5$), 1820, 1785 and 1735 (C=O); NMR (Silanor C, δ from TMS) 7.3–7.6 (m, $C_6H_5$—), 5.3–5.4 (d, —O—$CH_2$—), 4.9–5.1 (t, O=C—C$\underline{H}$—N), 2.9 (s, O=C—$CH_2$—$CH_2$—C=O), 2.3–2.8 (m, O=C—C$\underline{H}_2$—$CH_2$CH—).

Example 16. N-Cbz-L-pyroglutamylcyanamide (13)

Cbz-L-pyroglutamic acid N-hydroxysuccinimide ester (1.8 g, 5.0 mmol) in 40 ml of THF was added drop-wise to a solution of sodium cyanamide (0.96 g, 0.015 mol) in 30 ml of distilled water at ice bath temperature. The reaction was allowed to proceed at this temperature for 4 hours and the reaction mixture was then extracted with ethyl acetate (2×50 ml). The aqueous layer (pH 11) was separated and acidified to pH 2 with 2N HCl. The resulting white precipitate was filtered and dried to give 0.66 g (45.9% yield) of 13 as a white powder, mp 185°–186° C. (turned slightly yellow >170° C.). $[\alpha]_D^{23}$ −31.56° (c 1.0, $CH_3CN$); TLC: $R_f$=0.5 in $CH_2Cl_2$/MeOH/AcOH (80:20:5), detected by UV quenching and gradual development of yellow color with ferricyanide spray reagent; IR (Nujol, cm$^{-1}$), 3160 (NH), 3050 ($C_6H_5$), 2240 (C≡N), 1775 and 1725 (C=O); NMR (acetone-$d_6$, δ from TMS) 7.4 (s, $C_6H_5$), 5.3 (s, —$CH_2$—O—), 4.8–5.0 (m, O=C—C$\underline{H}$—N), 2.2–3.0 (m, $\overline{O}$=C—$CH_2$—$CH_2$—CH). Anal. Calcd for $C_{14}H_{13}N_3O_4$: C, 58.53; H, 4.56; N, 14.63. Found: C, 58.33; H, 4.73; N, 14.63.

Example 17. L-Pyroglutamic Acid N-Hydroxysuccinimide Ester

DCC (4.13 g, 0.020 mol) and N-hydroxysuccinimide (2.3 g, 0.020 mol) were added to a solution of L-pyroglutamic acid (2.58 g, 0.020 mol) in 50 ml of THF and 5 ml of dimethyl formamide (DMF) at ice bath temperature. The reaction was allowed to proceed at room temperature for 48 hours. The reaction mixture was then filtered to remove the bulk of the DCU and the filtrate was evaportaed in vacuo to dryness. The resulting white solid residue was dissolved in 40 ml of THF, the solution filtered, and the filtrate was evaporated in vacuo to give 5.61 g of semi-solid residue. This was crystallized from hot methylene chloride to give 2.35 g (crop 1) of white cyrstalline L-pyroglutamic acid N-hydroxysuccinimide ester. Additional product, 1.11 g (crop 2), was obtained from the filtrate giving a total yield of 76.5%. mp crop 1; 136°–137° C., crop 2; 134°–135° C.; TLC: $R_f=0.4$ in EtOAc/AcOH (100:1), detected by brown color development with N-chloro spray reagent.

Example 18. L-Pyroglutamyl-L-leucine Benzyl Ester

L-Pyroglutamic acid N-hydroxysuccinimide ester (4.52 g, 0.020 mol) was added to a solution of L-leucine benzyl ester (4.43 g, 0.020 mol) in 60 ml of THF at room temperature and the reaction was allowed to proceed for 15 hours. The reaction mixture was evaporated in vacuo to give a pale yellow liquid. This liquid was dissolved in methylene chloride (50 ml) and washed with 10% citric acid (50 ml) followed by 5% sodium bicarbonate (50 ml). The methylene chloride layer was dried over anhydrous sodium sulfate and evaporated in vacuo to give 6.37 g (95.8% yield) of crude product as a pale yellow, thick liquid. Crystallization from hot methylene chloride and petroleum ether gave 5.42 g (81.53% yield) of white crystalline compound, mp 127°–128° C. TLC: $R_f=0.58$ in EtOAc/AcOH (100:1), detected by UV quenching; NMR (Silanor C, δ from TMS) 7.34 (s, C$_6$H$_5$), 5.4 (s, —O—CH$_2$—C$_6$H$_5$—), 4.5–4.9 (m, —NH—CH—C=O), 3.9–4.3 (m, —NH—CH—C=O), 2.0–2.7 (m, cycl. —NH—CH$_2$—CH$_2$—CH), 1.4–1.8 (m, —CH$_2$—CH), 0.7–1.1 (fused d, —CH(CH$_3$)$_3$). Anal Calcd for C$_{18}$H$_{24}$N$_2$O$_4$: C, 65.04; H, 7.28; N, 8.43. Found: C, 65.32; H, 7.51; N, 8.36.

Example 19. L-Pyroglutamyl-L-leucine

L-Pyroglutamyl-L-leucine benzyl ester (6.65 g, 0.020 mol) was hydrogenated with 9% palladium on charcoal in 100 ml of methanol for 1 hour. The hydrogenation mixture was filtered through Celite and the filtrate was evaporated in vacuo to give 4.78 g of product as a white solid. This was crystallized from methanol and diethyl ether to give 4.63 g (95.6% yield) of white crystals, mp 152°–154° C. [reported mp 151°–152° C.]; $[\alpha]_D^{23}$ C. −19.35° (c 1.0, MeOH); TLC: $R_f=0.57$ in CHCl$_3$/MeOH/AcOH (80:20:5), detected by brown color development with N-chloro spray reagent; NMR (methanol-d$_4$, δ from TMS) 4.3–4.6 (m, —NH—CH—C=O), 4.1–4.3 (q, —NH—CH—C=O), 1.9–2.6 (m, cycl. O=C—CH$_2$—CH$_2$—CH), 1.5–1.8 (m, —CH$_2$—CH), 0.7–1.1 (m, —CH(CH$_3$)$_3$) Anal. Calcd for C$_{11}$H$_{18}$N$_3$O$_4$: C, 54.53; H, 7.49; N, 11.56. Found: C, 54.55; H, 7.39; N, 11.58.

Example 20. L-Pyroglutamyl-L-leucylcyanamide (14)

L-Pyroglutamyl-L-leucine (1.21 g, 5.0 mmol) was stirred with DCC (1.03 g, 5.0 mmol) and N-hydroxysuccinimide (0.58 g, 5.0 mmol) in 150 ml of THF, initially at ice bath temperature, then at room temperature overnight. The reaction mixture was filtered and the solvent was removed in vacuo to dryness. The residue was redissolved in THF and filtered. The filtrate (70 ml) was added drop-wise to a solution of sodium cyanamide (0.64 g, 0.010 mol) in 70 ml of distilled water at ice bath temperature. The reaction was allowed to proceed at this temperature for 4 hours. The reaction mixture was concentrated in vacuo to half its original volume at 25° C. and filtered. The filtrate (pH 7.5) was neutralized to pH 7 with 10% HCl and applied to an AG 1×2 anion exchange resin column (15×2 cm, 100–200 mesh, acetate form) packed with distilled water. The column was washed with water (380 ml) until no more cyanamide was detected by spotting on TLC plates (purple color with ferricyanide spray reagent), then eluted with a linear pH gradient consisting of equal volume of 0.15N HCl in the reservoir and water in the mixing flask (1000 ml:1000 ml). A total of 45×20 ml fractions were collected. The fractions containing the desired product (orange color when spotted on TLC plates and sprayed with ferricyanide reagent) were pooled and extracted with EtOAc/THF (5:1)(2×30 ml) and EtOAc (4×30 ml). The organic extract was dried over anhydrous sodium sulfate and evaporated in vacuo to dryness. The resulting solids were collected to give 1.29 g (96.9% yield) of crude product as white powder. A portion of the product (140 mg) was dissolved in methanol and applied on 4 preparative TLC plates (Preadsorbent, Analtech, 1000 u thickness) then eluted with CHCl$_3$/MeOH/AcOH (80:20:5). The bands which corresponded to the desired product were removed, extracted with ETOAc/absolute EtOH (2:1), and the extract was then filtered. The filtrate was evaporated in vacuo to dryness, the residue triturated with diethyl ether, and the product collected and dried in vacuo to give 79 mg (54.7% total yield) of off-white powder, mp dec. >175° C. (gradually turns yellow, then to a dark brown residue at 205° C.). $[\alpha]_D^{23}$ −29.93° (c 1.0, MeOH); TLC: $R_f=0.36$ in CHCl$_3$/MeOH/AcOH (80:20:5) detected by UV quenching (weak), orange color with ferricyanide spray reagent, and brown color with N-Cl spray reagent; IR (Nujol, cm$^{-1}$) 3300 (NH), 2170 (C≡N), 1670–1690 (C=O); NMR (methanol-d$_4$, δ from TMS) 4.1–4.6 (m, —NH—CH—C=O), 2.1–2.6 (m, cycl. —CH$_2$—CH$_2$—), 1.4–1.8 (m, —CH$_2$—CH), 0.8–1.1 (m, —CH(CH$_3$)$_2$).

Example 21. L-Pyroglutamyl-L-phenylalanine Methyl Ester

N-Methylmorpholine (2.02 g, 0.020 mol) and isobutyl chloroformate (2.73 g, 0.020 mol) were added to a solution of L-pyroglutamic acid (2.58 g, 0.020 mol) in 100 ml of THF/DMF (6:1) at −15° C. After a 2 minute coupling period, a mixture of L-phenylalanine methyl ester hydrochloride (4.31 g, 0.020 mol) (suspension) and N-methyl morpholine (2.02 g, 0.020 mol) in 50 ml of DMF was added to the reaction mixture. The reaction was allowed to proceed at this temperature for 30 minutes and then at room temperature for 1 additional hour. The reaction mixture was then filtered to remove fines and the filtrate was evaporated in vacuo to incipient dryness. The resulting yellow liquid was dissolved in 100 ml of ethyl acetate, and the ethyl acetate solution was washed with 5% citric acid saturated with sodium chloride (50 ml) and 5% sodium bicarbonate saturated with NaCl (50 ml). The separated organic layer was dried over anhydrous sodium sulfate and evaporated in vacuo to yield quantitative amounts of a pale yellow liquid which was used directly for the following step. TLC: $R_f$=0.22 in EtOAc/AcOH (100:1), detected by UV quenching; IR (neat, cm$^{-1}$) 3300 (NH), 3020-3060 ($C_6H_5$), 2860-2960 (alkyl), 1650-1750 (C=O); NMR (Silanor C, δ from TMS) 7.25 (fused s, $C_6H_5$—), 5.5-5.7 and 6.6-6.8 (broad, N$\underline{H}$'s), 4.6-5.1 (q, —NH—C$\underline{H}$—C=O), 3.0-3.2 (q, —C$\underline{H}_2$—$C_6H_5$), 1.6-2.5 (m, cycl. O=C—C$\underline{H}_2$—C$\underline{H}_2$).

Example 22. L-Pyroglutamyl-L-phenylalanine

L-Pyroglutamyl-L-phenylalanine methyl ester (1.27 g, 4.4 mmol) in 50 ml of methanol was stirred with 10% NaOH (1.93 ml, 0.193 g of NaOH, 4.8 mmol) at room temperature for 1 hour. The reaction mixture was evaporated in vacuo to dryness, the residue then dissolved in distilled water and the mixture extracted with ethyl acetate (100 ml). The aqueous layer (pH 10.5) was separated, acidified to pH 2 with 10% HCl, then saturated with sodium chloride and extracted with ethyl acetate (6×50 ml). The pooled ethyl acetate extract was dried over anhydrous sodium sulfate, filtered, and the filtrate was evaporated in vacuo to give a white foamy solid residue. This was triturated with anhydrous diethyl ether, collected, and dried in vacuo to give 1.04 g (86.0% yield) of white powder which was used directly for the following step. Mp 128°-130° C.; $[α]_D^{23}$ +13.51 (c 1.0, MeOH); TLC: $R_f$=0.66 in CHCl$_3$/MeOH/AcOH (80:20:5), detected by UV quenching and brown color with N-Cl spray reagent; NMR (methanol-d$_4$, δ from TMS) 7.22 (s, $C_6\underline{H}_5$—), 4.6-4.8 (m, —NH—C$\underline{H}$—C=O), 4.0-4.2 (q, —NH—C$\underline{H}$—C=O), 2.8-3.2 (m, —C$\underline{H}_2$—$C_6H_5$), 1.7-2.5 (m, cycl. O=C—C$\underline{H}_2$—C$\underline{H}_2$—C$\underline{H}$—).

Example 23.
L-Pyroglutamyl-L-phenylalanylcyanamide (15)

L-Pyroglutamyl-L-phenylalanine (4.10 g, 0.0148 mol) was allowed to react with DCC (3.37 g, 0.0163 mol) and N-hydroxysuccinimide (1.88 g, 0.0163 mol) in 60 ml of THF at ice bath temperature for 3 hours, and then at room temperature overnight. The reaction mixture was filtered and the filtrate was added drop-wise to a solution of sodium cyanamide (1.90 g, 0.0297 mol) in 60 ml of distilled water at ice bath temperature. The reaction was allowed to proceed at this temperature for 6 hours. The reaction mixture (pH 8) was then neutralized to pH 7 with 10% HCl, saturated with sodium chloride, and extracted with ethyl acetate (2×50 ml). The aqueous portion (pH 6.2) was acidified to pH 1.5 with 10% HCl and extracted with EtOAc/THF (3:1) (100 ml) and ethyl acetate (2×50 ml). The combined organic extract was dried over anhydrous sodium sulfate and evaporated in vacuo to give 4.20 g (94.5% yield) of crude product as an off-white solid residue. This was crystallized from abs. EtOH/diethyl ether to give 1.36 g (crop 1) of 15. The filtrate was concentrated and crystallized in the same manner to give 9.53 g (crop 2), giving a total yield of 42.5%. Mp 163°-165° C.; $[α]_D^{23}$ +7.81° (c 1.0, MeOH); TLC: $R_f$=0.29 in CHCl$_3$/MeOH/AcOH (80:20:5), detected by UV quenching and orange color with ferricyanide spray reagent; IR (Nujol, cm$^{-1}$) 3350 (NH), 3020 ($C_6H_5$), 2160 (C≡N), 1650-1690 (C=O); NMR (methanol-d$_4$, δ from TMS) 7.22 (s, —$C_6\underline{H}_5$), 4.5-4.7 (q, —NH—C$\underline{H}$—C=O), 4.0-4.2 (m, —NH—C$\underline{H}$—C=O), 2.8-3.2 (m, —C$\underline{H}_2$—$C_6H_5$), 1.7-2.6 (m, cycl. O=C—C$\underline{H}_2$—C$\underline{H}_2$—) Anal. Calcd for $C_{15}H_{16}N_4O_3$: C, 59.99; H, 5.37; N, 18.66. Found: C, 59.61; H, 5.61; N, 18.40.

II. Evaluation of Acylated Cyanamides In Vivo.

Compounds 1-11 were evaluated in rats for their ability to elevate and maintain blood acetaldehyde (AcH) levels following ethanol administration employing the methodology outlined in Table I.

TABLE I

A. Initial Screen Protocol

1. Drug Dose: 1.0 mmol/kg (ip)
2. Animals: Male rats of Sprague-Dawley descent (BioLab, Inc., St. Paul, Min.), weighing 185-225 g were used. Four animals were used for each drug administration protocol.
3. Timing: Animals were fasted beginning at 7:00 or 8:00 AM. One group of rats were administered the prodrug at 5:00 PM (zero time) and ethanol (2 g/kg, ip) at 8:00 AM (15 hours), and the animals were sacrificed at 9:00 AM (16 hours). A second set of rats received the prodrug at 6:30 AM (zero time) and ethanol at 8:30 AM (2 hours) and the animals were sacrificed at 9:30 AM (3 hours). Cyanamide treated animals (1.0 mmol/kg) served as positive control. Blood AcH levels were determined as described hereinbelow.

B. Time Course Protocol

1. Drug Dose: 0.5 mmol/kg (ip); 1.0 mmol/kg (po)
2. Animals: Male rats of Sprague-Dawley descent (BioLab, Inc., St. Paul, Min.), weighing 176-200 g were used. Two animals were used for each drug administration protocol.
3. Timing: Overnight fasted animals were administered the prodrug at zero time, ethanol (2 g/kg, ip) at 1, 4, 11, 23, 35, 47 and 71 hours and sacrificed 1 hour subsequent to each ethanol administration. Cyanamide treated animals (1.0 mmol/kg) served as positive control.

Blood AcH levels were measured 1 hour after ethanol (2 g/kg, ip) in treated and control animals essentially as described by Shirota et al., in J. Med Chem., 23, 669 (1980). The animal was stunned by a quick blow to the head and blood was immediately withdrawn by open chest cardiac puncture. Aliquots (0.2 ml) were placed in 20 ml serum vials containing 1.0 ml of 5 mM sodium azide (to minimize the artifactual generation of AcH from ethanol), and the vials immediately capped with a rubber septum, frozen on Dry Ice, and kept frozen at −20° C. until assayed. AcH was determined in duplicate by the head-space gas chromatographic procedure previously described by Nagasawa et al., in *Life Sci.*, 20, 187 (1977), and quantitated using a standard curve based on standards with known concentrations of AcH. The results of this study are summarized in FIGS. 1-4.

Cyanamide, a known potent AlDH inhibitor and positive control, elevated blood AcH 150-fold over drug-free controls at 3 hours, and more than 25-fold over controls at 16 hours post-drug administration. Sodium acetylcyanamide (1), the salt of the major urinary metabolite of cyanamide, was, as expected, much weaker than cyanamide in the elevation of ethanol-derived blood AcH; however, the compound still significantly elevated blood AcH at 3 hours (25-fold over controls). Benzoylcyanamide (2) displayed similar activity to 1 giving rise to slightly more elevation of blood AcH (10-fold over controls) at 16 hours than 1.

n-Butyrylcyanamide (3), with a four-carbon aliphatic acyl group, was found to be a short-acting AlDH inhibitor and was even more potent than cyanamide itself. The compound elevated blood AcH 170-fold over controls at 3 hours; however, AcH blood levels were rapidly reduced to approximately 20-fold over control levels at 16 hours. Pivaloylcyanamide (4) and 1-adamantoylcyanamide (5), which were designed to retard the rate of hydrolysis of the acylcyanamide linkage by attaching sterically bulky substituents on the carbonyl group, were found to be very potent, but short acting.

Palmitoylcyanamide (6) and stearoylcyanamide (7), two aliphatic fatty acylcyanamides, were almost as potent as cyanamide at 3 hours, and significantly higher blood AcH still prevailed at 16 hours, viz, 100-fold, and more than 50-fold over controls, respectively.

Pretreatment of rats with N-carbobenzoxycyanamide (8) followed by ethanol elevated to blood AcH levels 120-fold over controls at 3 hours, indicating that the carbobenzoxy group must have been cleaved effectively by an enzymatic process. N-Cbz-glycylcyanamide (9) also elevated blood AcH more than 80-fold over controls at 3 hours; however blood AcH was reduced to almost control levels at 16 hours. N-Cbz-glycyl-L-leucyl-cyanamide (12) was more potent than (9) at 3 hours, but like the latter, did not maintain significantly elevated blood AcH level at 16 hours.

Hippurylcyanamide (10) was less potent than N-benzoyl-L-leucylcyanamide (11), probably because 10 is a poorer substrate for leucine aminopeptidase than is 11. These compounds not only elevated blood AcH levels at 3 hours, but were also long-acting with significant levels of blood AcH present at 16 hours.

N-Cbz-L-pyroglutamylcyanamide (13) and L-pyroglutamyl-L-leucyl-cyanamide (14) were not nearly as potent as the other prodrugs. Unlike 14, L-pyroglutamyl-L-phenylalanylcyanamide (15) was found to be a very potent inhibitor of AlDH in vivo, giving rise to blood levels which were more than 110-fold higher than control levels at 3 hours.

Based on the above results, compounds 6, 7, 10 and 11 were selected for further studies in vivo. Their duration of effectiveness in elevating blood AcH was evaluated over a 72-hour time course according to the protocol described hereinabove.

Figure 5:
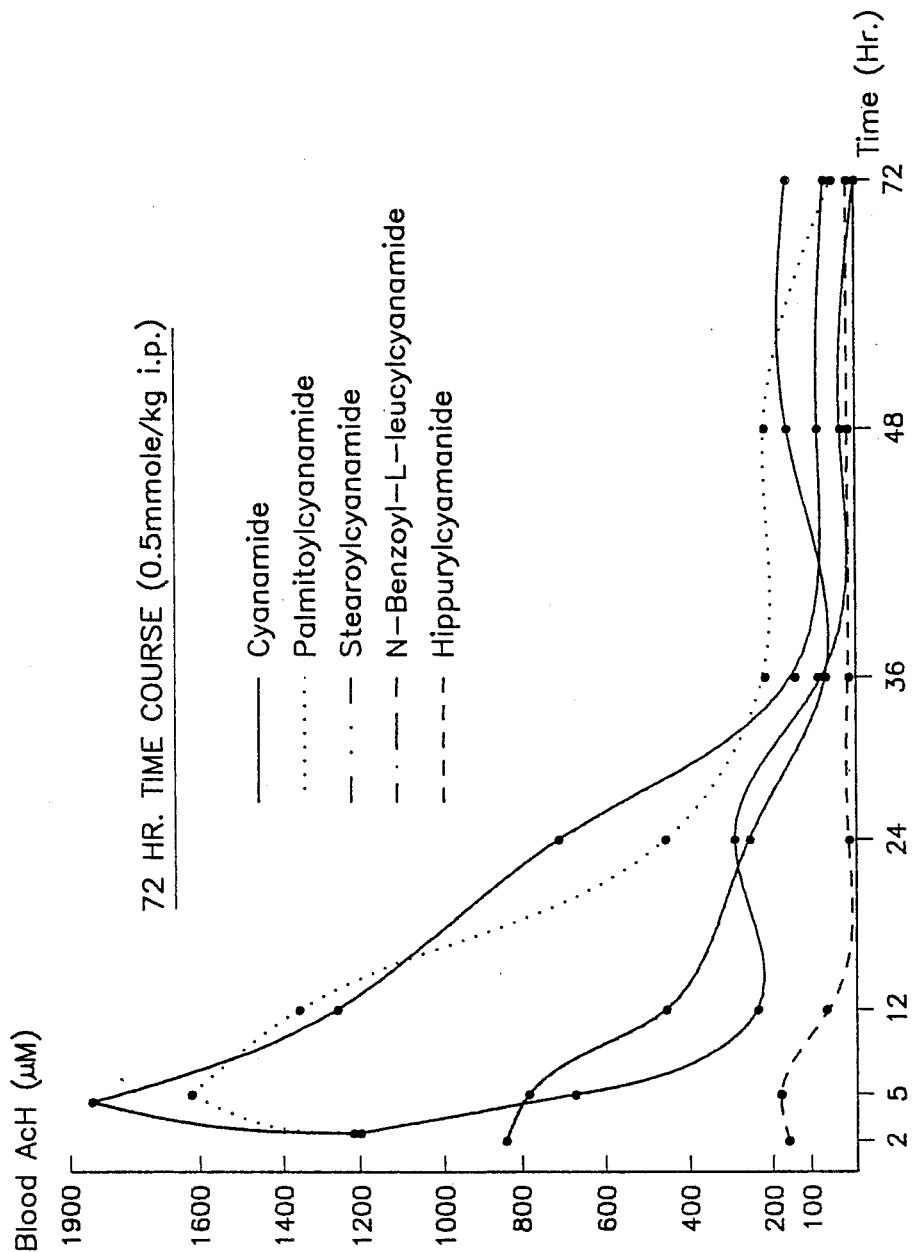
FIG. 5 is a graphic depiction of the effectiveness of four of the compositions of the invention in elevating blood AcH following ethanol administration in rats over a 72 hour time course (0.5 mmol/kg i.p. dose).

As shown in FIG. 5, blood AcH elevation by cyanamide reached a maximum within 2 hours, then the levels fell rapidly almost to control values at 36 hours. When palmitoylcyanamide (6) and stearoylcyanamide (7) were preadministered before ethanol, blood AcH levels reached their maxima at around 5 hours, then gradually fell, but the blood AcH elicited by 6 was significantly elevated even at 48 hours. Hippurylcyanamide (10) failed to maintain elevated blood AcH past 12 hours. In contrast, N-benzoyl-L-leucylcyanamide (11) initially elevated the blood AcH level less than cyanamide at 2 hours, but this compound continued to maintain elevated blood AcH even at 72 hours.

Figure 6:
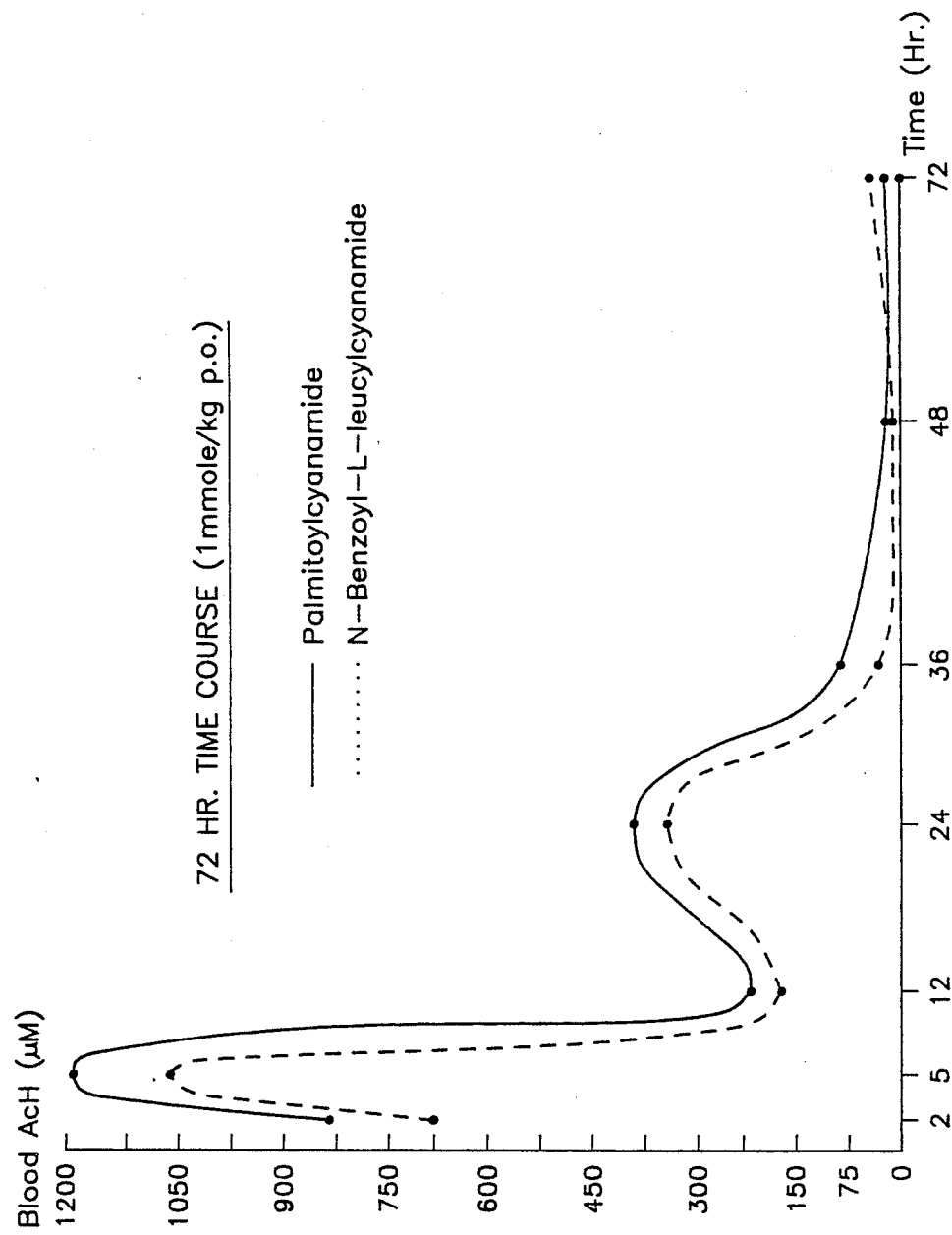
FIG. 6 is a graphic depiction of the effectiveness of palmitoylcyanamide and N-benzoyl-L-leucylcyanamide, administered orally, in elevating blood AcH following ethanol administration in rats over a 72 hour time course.

When 6 and 11 were administered by the oral route, both compounds gave similar blood AcH elevation curves, i.e., maximum AcH levels were seen at 2 hours, the AcH levels rapidly decreased to a trough at 12 hours, then once again increased at 24 hours (FIG. 6). Blood AcH then gradually fell back to control levels at around 36 hours.

Thus, a wide variety of acylated cyanamide analogs have been demonstrated to be effective to substantially raise mammalian blood AcH levels in the presence of ethanol. A number of the analogs of the present invention produced higher initial AcH levels and/or maintained the elevated AcH levels for longer periods of time than those produced by cyanamide itself. However, even relatively less-potent or short-acting compounds may be clinically useful as alcohol deterrent agents if they are found to be more specifically-acting than cyanamide itself, and/or are formulated appropriately.

The invention has been described with reference to various specific and preferred embodiments and techniques. However, it should be understood that many variations and modifications may be made while remaining within the spirit and scope of the invention.

What is claimed is:
1. Pivaloylcyanamide.
2. 1-Adamantoylcyanamide.

* * * * *

UNITED STATES PATENT AND TRADEMARK OFFICE
CERTIFICATE OF CORRECTION

PATENT NO. : 4,940,816

DATED : July 10, 1990

INVENTOR(S) : Nagasawa et al.

It is certified that error appears in the above-identified patent and that said Letters Patent is hereby corrected as shown below:

Column 3, line 36, delete "," after the figure "$C_{30}$";

Column 3, line 36, insert --(alkyl),-- after the figure "$C_{30}$";

Column 8, line 61, "$C_6\underline{H}$--)" should be --$C_6\underline{H}_5$)--.

Signed and Sealed this

Seventh Day of January, 1992

Attest:

HARRY F. MANBECK, JR.

*Attesting Officer*   Commissioner of Patents and Trademarks